United States Patent [19]

Stokowski et al.

[11] Patent Number: 4,998,019
[45] Date of Patent: Mar. 5, 1991

[54] PHOTOEMISSION CONTAMINANT DETECTOR

[75] Inventors: Stanley Stokowski, Danville; David Wolze, San Jose; Armand P. Neukermans, Palo Alto, all of Calif.

[73] Assignee: Tencor Instruments, Mountain View, Calif.

[21] Appl. No.: 416,763

[22] Filed: Oct. 3, 1989

[51] Int. Cl.$^5$ .............................................. G01N 21/89
[52] U.S. Cl. .............................. 250/360.1; 250/358.1; 250/372
[58] Field of Search .................. 250/358.1, 360.1, 372, 250/307

[56] References Cited

U.S. PATENT DOCUMENTS 4,590,376  5/1986  Smith .................................. 250/372
4,691,310  9/1987  Wine .................................... 369/50

OTHER PUBLICATIONS

T. Smith, "Photoelectron Emission from Aluminum and Nickel Measured in Air", *Jour. Apply. Phys.*, vol. 46, No. 4, Apr. 1975, pp. 1553–1558.
B. Quiniou et al., "Photoemissive Scanning Microscopy of Doped Regions on Semiconductor Surfaces", *Appl. Phys. Lett.*, vol. 55, No. 5, Jul. 31, 1989, pp. 481–483.

*Primary Examiner*—Carolyn E. Fields
*Assistant Examiner*—Drew A. Dunn
*Attorney, Agent, or Firm*—Thomas Schneck

[57] ABSTRACT

Methods for determining the presence or absence of, and the thickness or other spacial extent of, a contaminant layer at each of a plurality of two or more sites on the surface of an electrically conductive material such as a semiconductor, a metal or a metal silicide. The invention uses a change in photoemission current from an illuminated spot on the surface to determine the presence and extent of a contaminant layer at the illuminated site. Compensation is provided for the effects of capacitive current and photovoltaic current. The invention provides a pattern of illumination sites on the conductor surface that can, if desired, cover all points on the surface.

36 Claims, 5 Drawing Sheets

PHOTOEMISSION CONTAMINANT DETECTOR

FIELD OF THE INVENTION

This invention relates to measurement of contaminants by photoelectron emission stimulated by light.

BACKGROUND OF THE INVENTION

Contaminating layers, ranging in thickness from a few Angstroms to perhaps 100 Angstroms, that are present on the surface of an electrically conducting material such as a semiconductor material, a silicide or a metal, are increasingly important in the processing of chips containing integrated circuits. These contaminants may include native oxides on bare silicon or other semiconductor material, native or grown oxides on polysilicon, photoresist smudges on wafers, and organic coatings produced on the wafer through diffusion from other surfaces or through adhesion.

The presence of these contaminating layers often introduces unacceptable uncertainties in performance of the circuits on the chip. For example, the presence of an oxide on a polysilicon surface can drastically interfere with adhesion of subsequently deposited layers such as silicides and can cause peeling of these layers from the adjacent polysilicon. The presence of a native oxide on bare silicon can produce a contact resistance that significantly reduces the electrical current flowing from or to such a layer.

Quantitative information on these contaminants can often be made on bare silicon, providing the locations of the contaminants are known and contaminant thickness exceeds a few tens of Angstroms. However, these measurements, whether obtained through ellipsometry or reflectometry, are quite time consuming because each measurement gives information on a very small illuminated spot. If the contamination is not uniform over the surface of the wafer, it becomes very time consuming to provide an accurate map of the extent of contamination over the entire surface.

Additionally, the surface roughness of the substrate or other layer being examined can mask the presence of thin contamination layers, where ellipsometry or reflectometry is used to provide quantitative measurements. For example, ellipsometry studies must invoke the presence of an "interlayer" of unknown composition to account for the discrepancy between theoretical predictions and experimental results, although these interlayers are never seen in transmission electron microscopy photographs. Further, the sensitivity of such methods tends to decrease when the layers are only a few Angstroms thick because the interference effects are then quite small.

Other methods of examination of characteristics of substrate material that is adjacent to a substrate surface have been disclosed. Smith in Jour. Appl. Phys. 46 (1975) pp. 1553-1558, reviews many of these methods and discloses the use of photoelectron emission from aluminum and from nickel that has or may have an oxide film formed on an exposed surface of the metal. For oxide films, such as NiO, that are photoemitting themselves, photoelectron emission includes current generated within the metal and current generated within the oxide film. For other oxide films, such as $Al_2O_3$, that are not photoemitting, photoelectron current emission comes primarily from the metal, with the oxide providing a mask therefor. Most oxides of interest are not photoemitting.

Quiniou et al., in Appl. Phys. Lett. 55 (1989) pp. 481-483, disclose the use of photoemission to perform scanning microscopy of doped regions on semiconductor surfaces. This method, the authors assert, can provide an in situ probe of doping levels or doping patterns immediately below the surface in a semiconductor wafer with a spatial resolution of a few wavelengths of the probing beam. A focused ultraviolet laser beam is scanned across the surface, and differences in surface properties within the wafer material are observed at such differences in emitted photoelectron current. The system disclosed by Quiniou et al. requires a pressure in the electron collector chamber of the order of $10^{-3}-10^{-1}$ Pascals and a bias voltage of the order of 70 volts or more and uses a laser beam for illumination of the surface.

The systems used by previous workers for monitoring photoelectron current emitted from or adjacent to a semiconductor surface suffer from a number of defects. Because of the bias maintained between the charged particle collector and the underlying wafer, any small change in distance of separation between the wafer and the collection electrode will induce a capacitive current, which may vary with time. Because the collection electrode is relatively large and the extraction voltages are also large, the induced capacitive current can be significantly larger than the photoelectron current to be measured. It is, therefore, desirable to provide a means of compensating for a capacitive current developed between the wafer and the collection electrode. This compensation means should be capable of monitoring capacitive current developed at any distance of separation of the wafer surface and the collection electrode and should be sufficiently small that the compensation means can be incorporated in the photoelectron current monitoring system.

Another disagreeable feature of photoelectron current monitoring systems of previous workers is that photovoltaic current may also be induced by light beam illumination and thus affect the output signal for current. Photovoltaic current can be induced in a semiconductor material for any photon energy that is appreciably greater than the energy gap $E_g$ for that material, and the energy gap is generally much less than the work function W for the material. For example, the work function or photoelectric threshold for bare silicon ranges from 4.60 to 5.11 eV, depending upon the crystal direction parallel to the incident light beam, but the energy gap in bare silicon is only 1.12 eV. If the photovoltaic current is uniform across the surface of the wafer, its effect on the photoelectron current arising from photoemission might be small and might be eliminated within the system. However, photovoltaic current is affected locally by dislocations and other defects in the semiconductor material Therefore, it is likely that the photovoltaic current induced will vary from site to site on the surface of the wafer. What is needed is means for compensating for the photovoltaic current at whatever light beam intensity is used. Preferably, this compensation means should be sufficiently small that it may be incorporated in the photoelectron current monitoring system.

SUMMARY OF THE INVENTION

These needs are met by a method for determining the presence and thickness, if any, of contaminants at each of a plurality of sites on the surface of an electrically conducting material. The method includes the steps of: (1) sequentially illuminating each site with a light beam having a wavelength component with photon energy greater than the work function of the material to allow photoelectrons to be liberated from the conducting material beneath the site; (2) providing electron collection means for determining the photoelectron current that emerges from the site; (3) compensating for capacitive current effects that arise from a change in separation distance between the semiconductor surface and the electron collection means; and (4) compensating for photovoltaic current effects that arise whenever the energy of the light beam photons is greater than the minimum energy $E_g$ required to raise an electron from a valence band to a conduction band. The steps (3) and (4) may be included or deleted independently of one another.

One technique for compensating for capacitive current effects is to provide a second electron collection means adjacent to the first electron collection means and spaced apart from the surface by the same distance, but with the second electron collection means not lying directly over the site illuminated. The second electron collection means senses only the capacitive current, if any, and if the currents sensed at the first and second electron collection means are subtracted from one another the effect of the capacitive current is subtracted out in the final signal.

One technique for compensating for photovoltaic current is to illuminate a surface site (1) by a first light beam having an energy that is appreciably greater than the work function of the conductor material and, (2) by a second light beam whose photon energy is appreciably less than the work function but exceeds the energy gap for production of photovoltaic current in the conductor material. The two light beams illuminate the surface site at different times, and the two current signals are subtracted from one another to remove the effects of the photovoltaic current in the resulting signal.

BEST MODE FOR CARRYING OUT THE INVENTION

Figure 1:
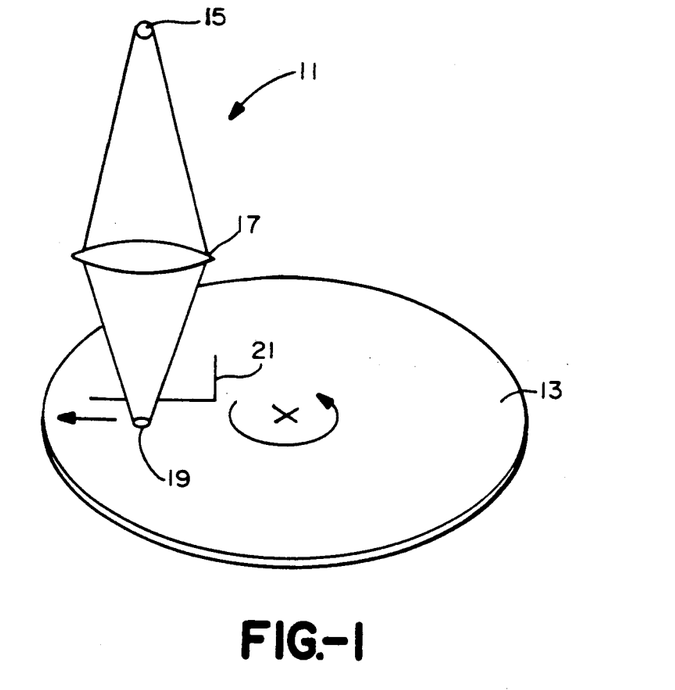
FIG. 1 is a perspective view illustrating illumination of different sites on a wafer surface by a light beam, where the position of the spot or trace of the light beam may be changed by translation and/or rotation of the wafer or of the trace of the light beam.

With reference to FIG. 1, a system 11 for monitoring photoelectron current developed at a site on a surface of a wafer 13 or other electrically conducting material will include a light source 15, a lens 17 or other optical element to receive the light beam and focus the beam to illuminate a site 19 on the wafer surface. An electron collector 21 is positioned above and adjacent to the site 19 in order to collect photoelectrons generated by the photoemissive action of the light beam in the wafer material immediately beneath the illuminated site 19. The wafer 13 may be rotated in the plane of its surface about a central point, and either the light beam system or the wafer may be translated relative to one another so that the illuminated site 19 is described by a light beam trace that moves around on the surface of the wafer 13. At each illumination site 19, a portion or all of that site may be covered by a contaminant, of unknown thickness or spacial extent. If a site 19 is illuminated, a substantial portion of the light beam energy is absorbed by atomic constituents that lie adjacent to and beneath the illuminated site in the electrically conducting material. If the light beam has a wavelength component with photon energy appreciably greater than the work function W of the material, photoelectrons will be liberated from the material by the well known photoemissive action in the conductive material 13. A portion of the photoelectrons thus liberated within this layer will be transported to the surface and through the contaminant, if any, present on the surface and will be collected by the electron collector 21 positioned immediately above the illumination site 19. If a contaminant layer overlies part or all of the illumination site on the surface of the conductive material 13, the photoelectron current sensed by the electron collector will be substantially reduced from the photoelectron current sensed in the absence of such contaminant layer. Thus, the photoelectron emission current is found to be strongly affected by the presence or absence of any contaminant layers that overlie the illumination site 19.

Figure 2:
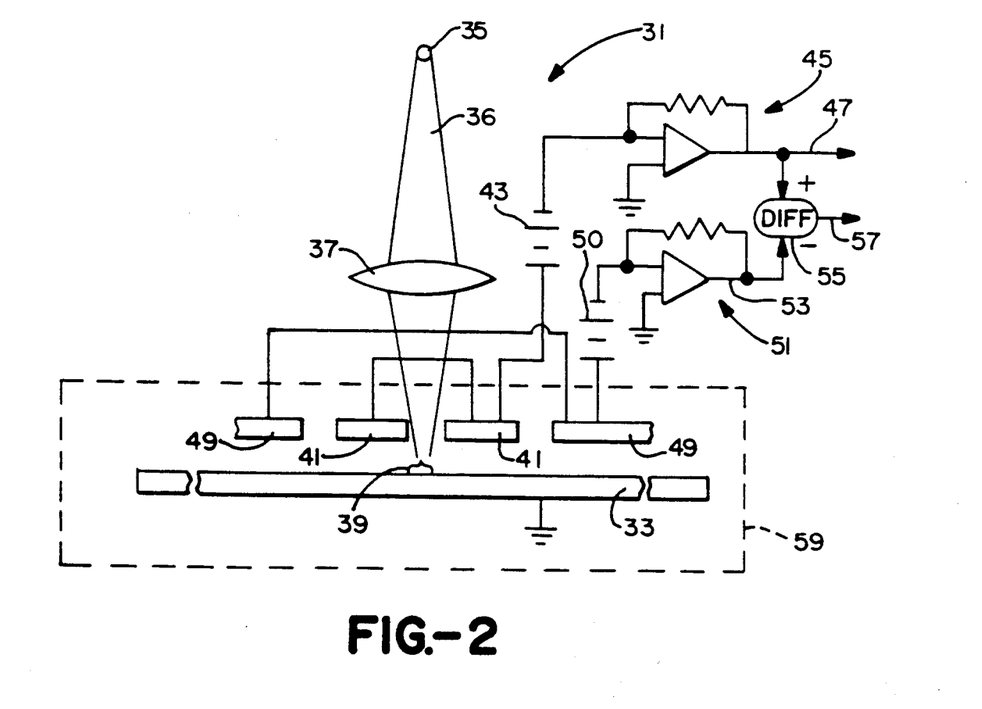
FIG. 2 is a schematic side view illustrating illumination of a surface site to eliminate the capacitive current effects according to the invention.

FIG. 2 illustrates a system for mapping the presence, and perhaps the thickness or other spatial extent, of contaminants lying on the surface of a conductive material at a plurality of sites on the surface. The system 31 includes a grounded layer 33 of electrically conductive material from which photoemission will occur, a source 35 of a light beam 36 that is focused by a lens 37 or other optical components to illuminate an illumination site 39 on the surface of the material 33. Photoemission from the material 33 occurs as discussed above, and a portion of the photoelectrons thus liberated are collected by a first electron collector 41 that is positioned adjacent to and overlying the illumination site 39. The first electron collector 41 may be an electrode that is transparent to the wavelength of the light beam 36 so that the electrode 41 may be a solid sheet of the electrode material. Alternatively, the first electron collector 41 may be a ring of electrode material with an aperture at the center through which the light beam 36 passes, as shown in FIG. 2. A positive voltage difference is imposed by a bias means 43 positioned between the first electron collector 41 and a current sensor for this collector. The photoelectron current produces a signal that is amplified by a first amplifier 45 and issues as a first output signal on a signal output line 47.

Capacitive current effects can arise when the distance of separation of the electron collector and the emitting surface changes with time. Capacitive current effects are compensated for in the system 31 shown in FIG. 2 by providing a second electron collector 49 that is positioned above the surface of the conductive material 33 with the same distance of separation as for the first electron collector 41. A positive voltage difference is imposed by a bias means 50 positioned between the second electron collector 49 and a current sensor for this collector. The second electron collector 49 is spaced apart from the first electron collector 41 so that the second electron collector overlies a portion of the surface that is not presently illuminated by the light beam 36. Thus, any current received by the second electron collector is likely due to capacitive effects only, and this contribution to total current will also be present in the current received by the first electron collector 41. The current received by the second electron collector 49 is amplified by an amplifier 51 and issues as a second output signal on a signal output line 53. A difference signal is formed by a difference module 55 from the two output signals that appear on the signal output lines 47 and 53, and this difference signal issues as the system output signal on an output signal line 57.

Optionally, an electrical shield 59 or other container may be provided that surrounds the wafer of electrically conducting material 33 and the first and second electron collectors 41 and 49. The interior of the shield or container 59 may contain a gas such as He, Ne, Ar, Kr, Xe or $N_2$, or another gas that does not contain oxygen and is relatively unlikely to permit electron attachment to the atoms or molecules of such gas. A gas that permits electron attachment to its atoms or molecules will develop a negative charge overall that will interfere with and reduce the photoelectron current collected at the electron collector. Thus, use of gases that do not have a relatively low likelihood of electron attachment thereto should be avoided. Gas pressures of the order of $10^{-1} - 10^5$ Pascals are acceptable here.

Figure 3:
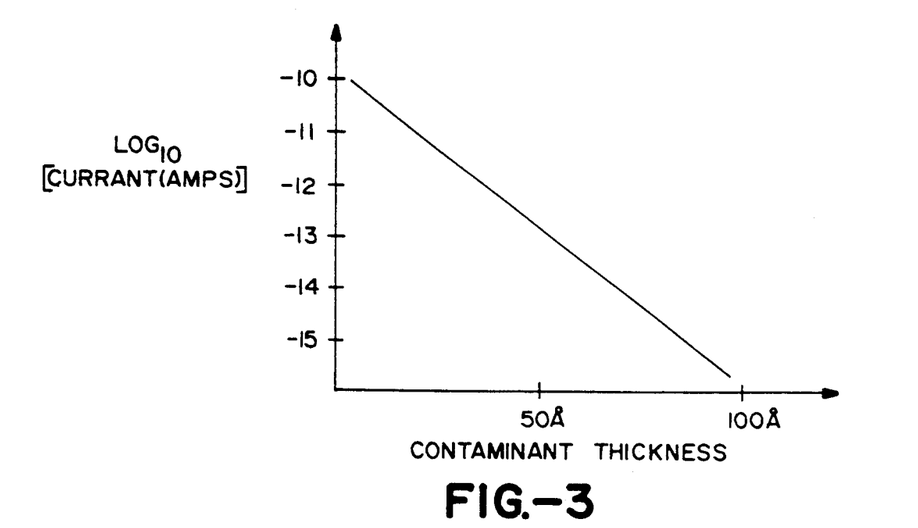
FIG. 3 is a graphic view illustrating the variation of photoelectron current with thickness of a contaminant present on the surface site being illuminated.

FIG. 3 graphically illustrates the decline in photoelectron current, expressed in amps, for an increase in the thickness of the contaminant layer through which the photoelectrons must pass before such electrons are collected at an electron collector. The photoelectron current can be reduced by four to six orders of magnitude by an increase in contaminant layer thickness of the order of 100 Å. The invention can be used to detect the presence of, and perhaps the thickness or other special extent of, a layer of contaminant present at a particular illumination site on the surface of a wafer.

Figure 4:
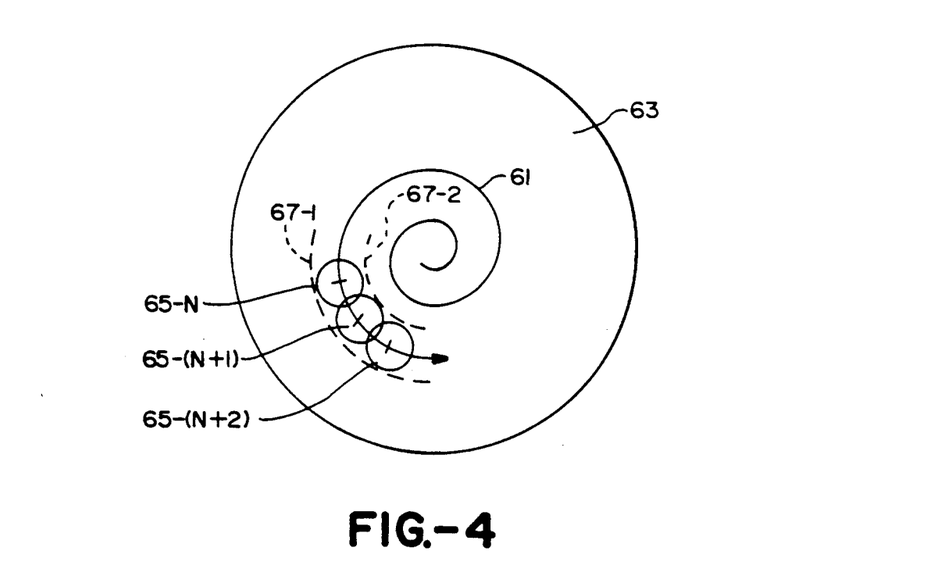
FIGS. 4 and 7 illustrate two possible paths for the light beam trace, a spiral pattern and a serpentine pattern, respectively, on the surface of the conductor material.

FIG. 4 illustrates a spiral path 61 that may be defined by the light beam trace on the surface of the wafer 63. In one embodiment, a plurality of discrete, approximately circular, light beam traces 65-N, 65-(N+1), 65-(N+2) that successively overlap along the spiral path 61 may be used as the illumination sites on the surface of the wafer 63. Alternatively, the discrete plurality of illumination sites may be replaced by a continuous band of such sites, indicated by the envelope defined by the two dotted lines 67-1 and 67-2 shown in FIG. 4.

If the spiral is defined by a radial coordinate dependence $r = r(\Theta) = r_1 \Theta$, where $\Theta$ is the angular coordinate in a plane, the light beam trace will move with approximately constant linear velocity on the surface if the time rate of change $\Theta$ of the angular coordinate and the radial coordinate r are related by the relation $$[r^2 + r_1^2]\Theta^2 = \text{constant}.$$

A light beam trace that moves with approximately constant linear velocity is preferred for all paths or patterns.

Figure 7:
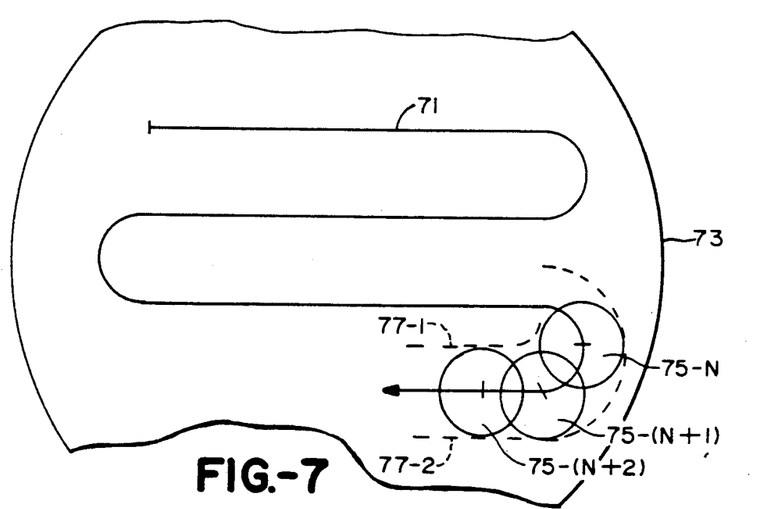

FIG. 7 illustrates the use of an alternative path, a serpentine path 71 that is laid down on the surface of a wafer 73 and winds back and forth in serpentine fashion to cover all the illumination sites on the surface. In FIG. 7, a plurality of discrete illumination sites 75-N, 75-(N+1), 75-(N+2) may be defined by the light beam trace as the projection of the light beam moves along the serpentine path 71. Alternatively, a continuous band of illumination sites may be used, defined by an envelope indicated by the two dotted curves 77-1 and 77-2 in FIG. 7. Using this continuous band alternative with the spiral pattern in FIG. 4 or with the serpentine pattern in FIG. 7, the photoelectron current signal received by the electron collector 41 in FIG. 2 would be a continuous set of signals, rather than the sequence of discrete signals that is received at the electron collector where a plurality of discrete illumination sites is provided on the surface.

Figure 5:
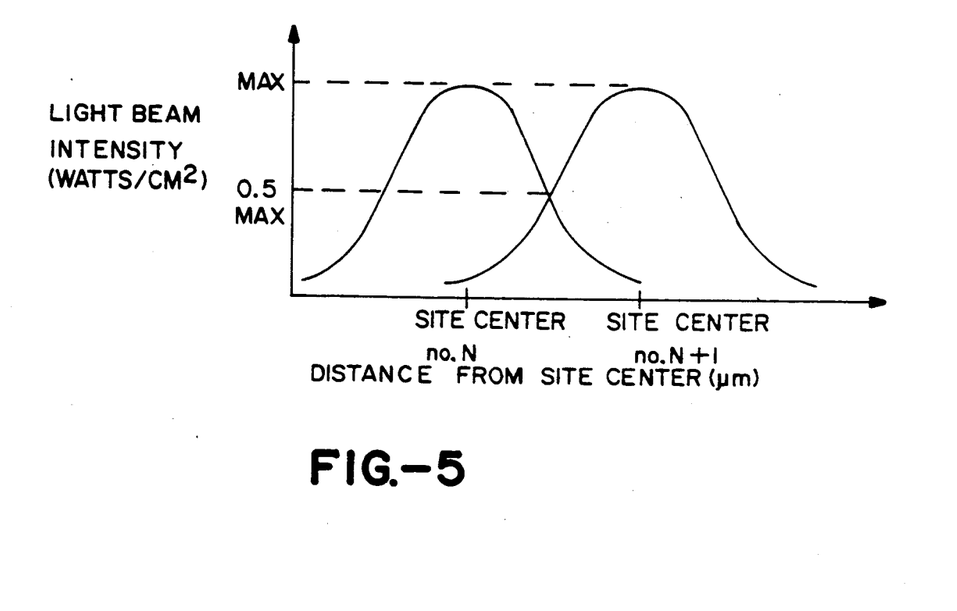
FIG. 5 is a graphic view showing relative intensity of two bell-shaped light beams that are centered at two adjacent sites on the surface.
Figure 6:
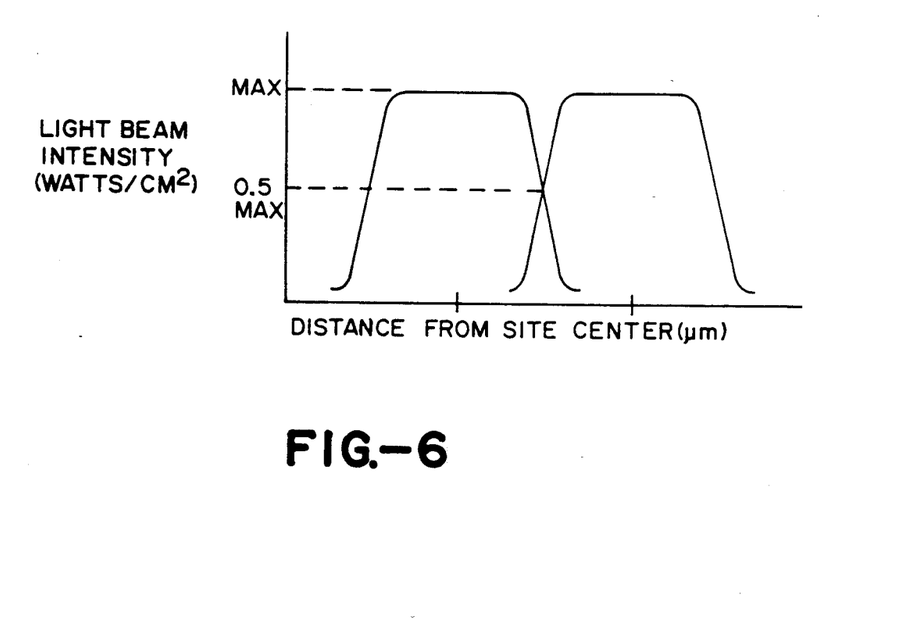
FIG. 6 is a graphic view illustrating the relative intensity of two top hat-shaped light beams centered at two adjacent sites on the surface.

If the entire wafer surface, or substantial portions thereof, is to be covered by the collection of illumination sites, the illumination sites must overlap on the portions of the surface to be thus covered. If the light beam has a standard Gaussian or bell shaped intensity as a function of radial distance from the center of the beam, two adjacent light beams, centered at illumination site centers no. N and N+1, will have the comparative intensity distributions shown in FIG. 5. Thus, it may be necessary to arrange for the light beams that illuminate two adjacent illumination sites to overlap sufficiently that the sum of their intensities in the overlap region is at least as large as the maximum intensity of either beam viewed in isolation. If the light beam used has a "tophat" shape, with the intensity decreasing very sharply from maximum intensity to approximately zero at a given radius, the light beam traces for two adjacent sites no. N and N+1 would again be overlapped so that the sum of their intensities in the region of overlap is at least equal to the maximum intensity of either light beam viewed in isolation. This is illustrated in FIG. 6 for two adjacent tophat light beam traces.

Figure 8:
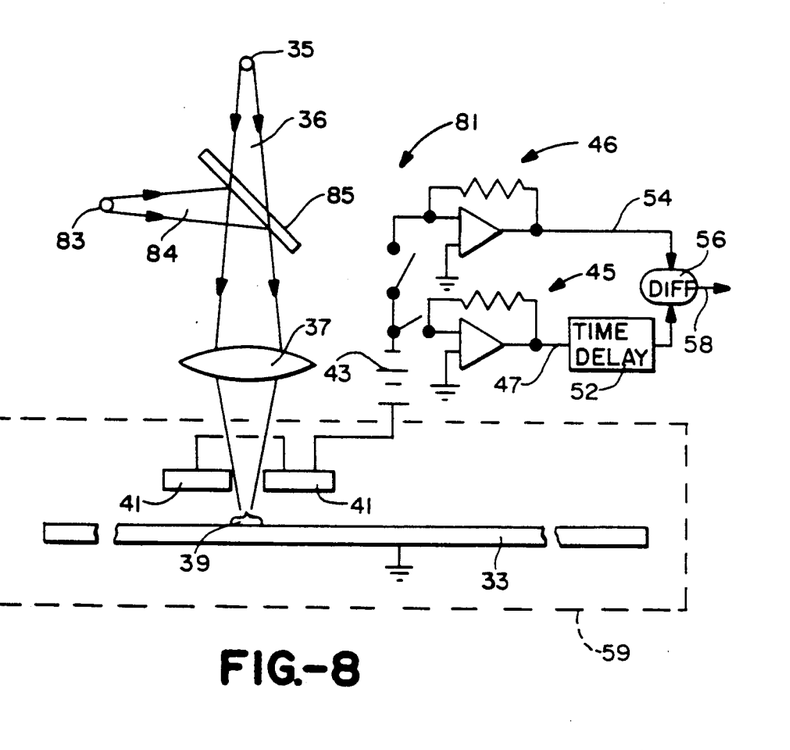
FIGS. 8 and 9 are two schematic side views illustrating two embodiments of the invention that compensates for photovoltaic current effects.

FIG. 8 illustrates an embodiment of the invention useful in determining the presence or thickness or other spatial extent of contaminants on a surface of the wafer 33, where the presence of photovoltaic current within the wafer material is to be compensated for. Photovoltaic current is developed within an electrically conducting material whenever the energy gap $E_g$ or difference between a conductivity band and an adjacent valence band is appreciably exceeded by the photon energy of a light beam used to illuminate the material. Thus, if the energy gap $E_g$ is less than the work function W of the material, a photon having an energy E satisfying the relation $E_g < E < W$ will produce photovoltaic current but will not produce photoemission current.

The system 81 shown in FIG. 8 includes a wafer 33 of electrically conducting material, a light source 35 that produces a first light beam 36 that is received by a lens 37 or other optical element and focused on the surface at one of the illumination sites 39. The photoelectrons produced by photoemissive action in the conductive material of the wafer 33 beneath the illumination site is collected at an electron collector 41 as before, where the electron collector is positioned immediately above the illumination site 39. A positive voltage difference between the electron collector 41 and a current sensor is impressed by a voltage difference or bias means 43 as shown. The photoelectron current received by the electron collector 41 is amplified by a system 45 and the output signal appears on a signal output line 47 as before. The light source 35 produces photons of energy greater than the work function W of the conductive material in the wafer 33. A second light source 83 produces a light beam 84 whose photons have energy greater than the energy gap $E_g$ of the wafer material but less than the work function W of the wafer material. The first light beam 36 is caused to pass through a semi-transparent mirror 85 before being received by the lens 37. The second light beam 84 is caused to be reflected from the semi-transparent mirror 85 and to then be received by the lens 37 for focusing thereof at the illumination site 39. The two light sources 35 and 83 are alternatingly activated and deactivated so that at most one of these light sources illuminates the illumination site 39 at any given time.

The current signal produced by the first light beam 36 is amplified by the circuit 45 and passes to a time delay module 52. The current signal produced by the second light beam 84 is amplified by the circuit 46 (and by the circuit 45) and issues on an output line 54 that is received by the negative input terminal of a difference-forming module 56. The positive input terminal of the module 56 receives the time delayed current signal from the time delay module 52 (the earlier current signal produced by the first light beam 36 at the same site). The module 56 subtracts the current signal on output line 54 form the time delayed signal issued on the output line 47 and issues the difference signal on an output line 58. Optionally, two switches may be included in the signal path that connects the electron collector 41 to the amplifiers 45 and 46, one switch for each amplifier input, so that at most one of these two amplifiers actively processes a signal from the electron collector at any particular time.

The electrical signal representing photoelectron current that is produced by the electron collector 41 consists of two alternating sequences of signals: (1) a first sequence, produced by the first light beam 36, consisting of the sum of the photoemission current and the photovoltaic current; and (2) a second sequence, produced by the second light beam 84, consisting only of the photovoltaic current. If the two light beams 36 and 84 are arranged to produce the same photovoltaic current at the illumination site 39, the difference of these two sequences of signals may be formed in order to subtract out the effect of the presence of the photovoltaic current, leaving only the photoemission current as an output signal.

Figure 9:
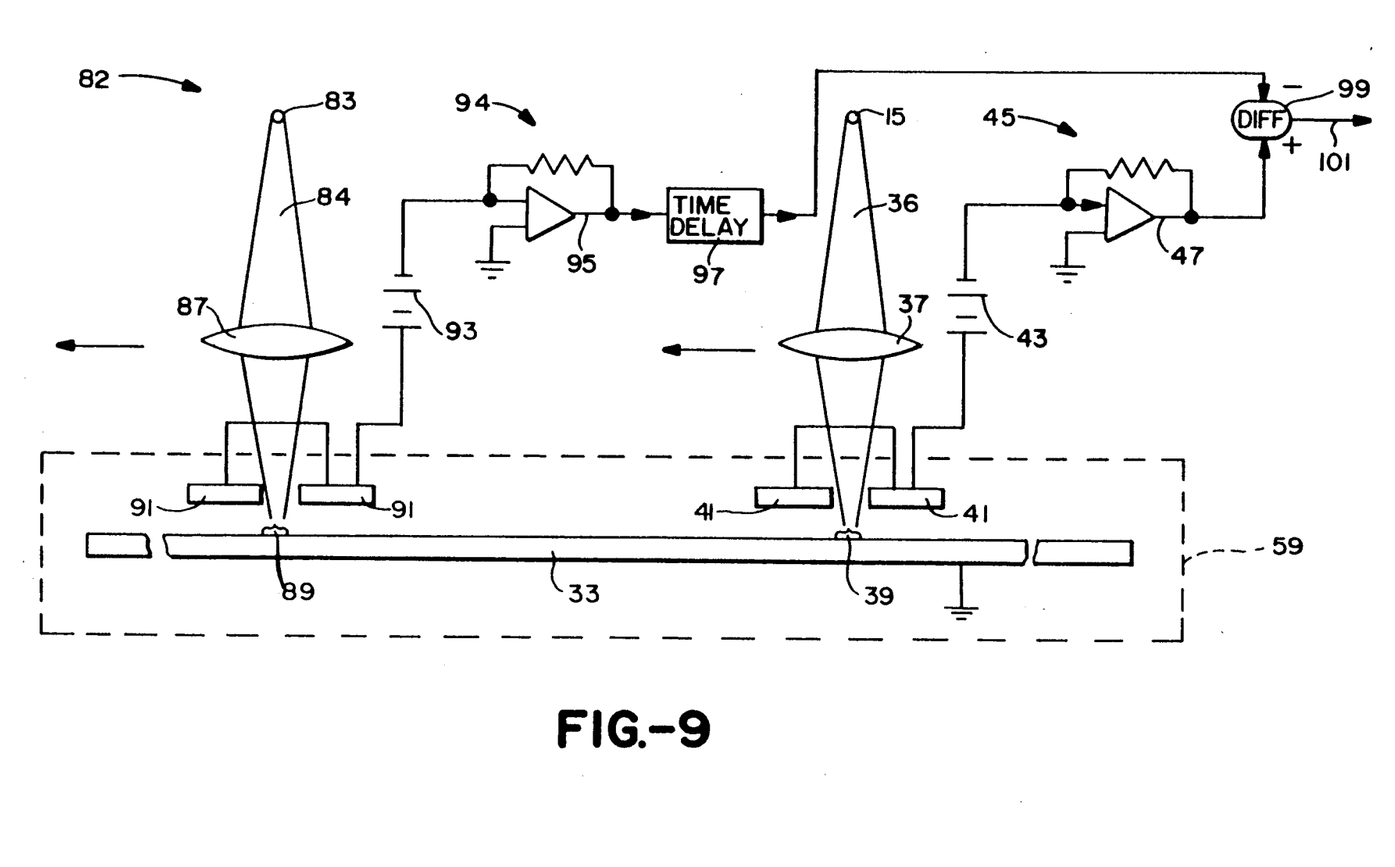

FIG. 9 illustrates another embodiment 82 of the invention where the presence of photovoltaic current is compensated for. In FIG. 9, the light source 83, which produces photons of energy greater than the gap energy $E_g$ but less than the electron work function W, illuminates a site 89 on the substrate, at a time assumed to be earlier than the time at which the light source 15 illuminates the site 39. The collection of sites illuminated by the light source 83 is assumed to be the same as the collection of sites illuminated by the light source 15. However, the light source 83 illuminates each of this collection of sites at an earlier time than the time such site is illuminated by the light source 15. The second light source 83 produces a light beam 84 that is focused by a second lens 87 or other light focusing means on the second site 89 on the substrate 33. Illumination of the site 89 by the light source 83 does not produce photoemission electrons but does produce photovoltaic current in the substrate 33, and this photovoltaic current is received by a second electron collector 91 that is positioned above and adjacent to the second site 89. The total intensity of the light sources 15 and 83 should be adjusted to produce the same photovoltaic current under the same conditions, as in FIG. 8. A positive voltage is impressed on the second electron collector 91 by a bias means 93 that is positioned between the electron collector 91 and a current sensor for this collector.

The current signal sensed by the collector 91 is passed through an amplifier 94 and appears on an output line 95 that is received by a time delay module 97. At a later time, when the light source 15 illuminates the site 89, the (time delayed) current signal for the site 89 is issued by the time delay module 97 and is subtracted from the current signal for the site 89 that appears on output line 47. This subtraction occurs in a difference module 99; and the output signal on output line 101 is the photoemission current sensed at the site 89, with the photovoltaic current removed therefrom.

Illumination of the second site 89 by the light source 83 may precede, rather than follow, illumination of the site 89 by the light source 15. In this situation, the current signal that issues on the output line 47 would be time delayed relative to the current signal that issues on the output line 95.

Light sources that are suitable for the first light source 35 in FIGS. 2, 8 or 9 include continuous, deep ultraviolet sources such as deuterium or mercury discharge lamps or lasers with emission wavelengths 0.4 $\mu$m. Laser fluence should be kept low at the illumination site to avoid photochemical decomposition or other chemical reactions that would otherwise be promoted at such site. The second light source 83 shown in FIGS. 8 and 9 should have a characteristic energy less than the work function of the wafer material but larger than the energy gap $E_g$ of such material. The second light source may be drawn from ultraviolet light sources and visible light sources with associated wavelengths below 1.1 $\mu$m for a silicon wafer material and below 0.85 $\mu$m for GaAs wafer material.

The electrically conductive material that forms the wafer may be drawn from semiconductor material such as silicon, germanium, gallium, arsenide and polysilicon; from metals such as aluminum, tungsten and molybdenum; and from metal silicides such as titanium silicide, platinum silicide, palladium silicide, cobalt silicide, zirconium silicide, tantalum silicide, hafnium silicide, niobium silicide, vanadium silicide, nickel silicide, tungsten silicide and molybdenum silicide. The resistivity of the metal silicides is generally quite low, usually under 100 ohm-cm. Any material with an electrical resistivity of no more than $10^6$ ohm-cm is a good candidate for the wafer material used in this invention.

We claim:

1. A method for determining the presence and the thickness, if any, of contaminants at each of a plurality of sites on a surface of an electrically conducting material, the method comprising the steps of:

sequentially illuminating each site with a light beam having a wavelength component that stimulates photoelectron emission from the conducting material that lies beneath each site;

providing electron collection means for determining the photoelectron current that emerges from the conducting material that lies beneath each site; and electrically compensating for capacitive current effects that arise from a change in separation distance between the surface and the electron collection means.

2. The method of claim 1, wherein said step of providing said electron collector means comprises the steps of:

providing an electron collector adjacent to and above said illuminated site to determine said photoelectron current; and providing a positive voltage difference between the electron collector and said electrically conducting material.

3. The method of claim 2, wherein said step of providing said positive voltage difference includes providing a voltage difference in the range of 5–100 volts for said electron detector relative to the voltage of said electrically conducting material.

4. The method of claim 2, wherein said step of compensating for said capacitive current effects comprises the steps of:

providing a second electron collector that is laterally spaced apart from said first electron collector and is spaced apart from said surface by approximately the same distance as the separation between said first electron collector and said surface;

providing a positive voltage difference between the second electron collector and said electrically conducting material that is equal to said positive voltage difference between said first electron collector and said surface; and subtracting the photoelectron current determined at the second electron collector from said photoelectron current determined at said first electron collector.

5. The method of claim 4, wherein said step of providing said second electron collector includes positioning said second electron detector so that it does not lie directly above said illuminated site.

6. The method of claim 1, wherein said step of sequentially illuminating each said site with a light beam comprises moving the trace of said light beam on said surface of said electrically conducting material so that the trace follows an approximately spiral pattern that sequentially illuminates each of said sites.

7. The method of claim 6, wherein said step of moving said light beam trace in an approximately spiral pattern includes moving said light beam trace with approximately constant linear velocity.

8. The method of claim 6, wherein said step of moving said light beam trace in an approximately spiral pattern includes moving said light beam trace to follow a curve on said surface defined by $$(r^2+r_1^2)\Theta^2 = \text{constant},$$

where said light beam trace has an associated angular velocity $\Theta$ and an associated radius $r$ and $r_1^2$ is a nonnegative constant.

9. The method of claim 1, wherein said step of sequentially illuminating each said site with a light beam comprises moving the trace of said light beam on said surface of said electrically conducting material so that the trace follows a serpentine pattern that sequentially illuminates each of said sites.

10. The method of claim 9, wherein said step of moving said light beam trace in an approximately serpentine pattern includes moving said light beam trace with approximately constant linear velocity.

11. The method of claim 1, further comprising the step of illuminating each of said sites for a time interval of at least one millisecond.

12. The method of claim 1, further comprising the step of providing said electrically conducting material from the class of materials with electrical resistivities of no more than $10^6$ ohm-cm that consists of silicon, germanium, gallium arsenide, polysilicon, aluminum, tungsten, molybdenum, titanium silicide, platinum silicide, palladium silicide, cobalt silicide, zirconium silicide, tantalum silicide, hafnium silicide, niobium silicide, vanadium silicide, nickel silicide, tungsten silicide and molybdenum silicide.

13. The method of claim 1, wherein said step of sequentially illuminating said sites includes providing a light beam with a light wavelength of at most 0.4 μm.

14. The method of claim 1, further comprising the step of providing an atmosphere above said surface of said electrically conducting material composed of a gas whose particles have a relatively low likelihood of electron attachment thereto.

15. The method of claim 14, wherein said step of providing an atmosphere includes providing said gas from the class of gases consisting of He, Ne, Ar, Kr, Xe and $N_2$.

16. The method of claim 1, wherein said step of illuminating said sites on said surface is performed by causing the light beam trace to define a continuous curve that passes through all of said sites.

17. The method of claim 1, further comprising the step of electrically compensating for photovoltaic current that arises through said illumination of said sites.

18. The method of claim 17, wherein the step of compensating for said photovoltaic current comprises the steps of:

sequentially illuminating each said site with a second light beam for which all wavelengths $\lambda$ thereof satisfy the relation $hc/W < \lambda < \lambda_g = hc/E_g$, where W is the electron work function and $E_g$ is the energy gap of said electrically conducting material;

illuminating each said site by said first light beam and by the second light beam in different time intervals that do not overlap; and for each said site, subtracting said photoelectron current, determined when the second light beam illuminates said site, from said photoelectron current, determined when said first light beam illuminates said site.

19. A method for determining the presence and the thickness, if any, of contaminants at each of a plurality of sites on a surface of an electrically conducting material, the method comprising the steps of:

sequentially illuminating each site with a light beam having a wavelength component that stimulates photoelectron emission from the conducting material that lies beneath each site;

providing electron collection means for determining the photoelectron current that emerges from the conducting material that lies beneath each site; and electrically compensating for photovoltaic current that arises through illumination of a site.

20. The method of claim 19, wherein the step of compensating for said photovoltaic current comprises the steps of:

sequentially illuminating each said site with a second light beam for which all wavelengths $\lambda$ thereof satisfy the relation $hc/W < \lambda < \lambda_g = hc/E_g$, where W is the electron work function and $E_g$ is the energy gap of said electrically conducting material;

illuminating each said site by said first light beam and by the second light beam in different time intervals that do not overlap; and for each said site, subtracting said photoelectron current, determined when the second light beam illuminates said site, from said photoelectron current, determined when said first light beam illuminates said site.

21. The method of claim 19, wherein said step of providing said electron collector means comprises the steps of:

providing an electron collector adjacent to and above said illuminated site to determine said photoelectron current; and providing a positive voltage difference between the electron collector and said electrically conducting material.

22. The method of claim 21, wherein said step of providing said positive voltage difference includes providing a voltage difference in the range of 5–100 volts for said electron detector relative to the voltage of said electrically conducting material.

23. The method of claim 19, wherein said step of sequentially illuminating each said site with a light beam comprises moving the trace of said light beam on said surface of said electrically conducting material so that the trace follows an approximately spiral pattern that sequentially illuminates each of said sites.

24. The method of claim 23, wherein said step of moving said light beam trace in an approximately spiral pattern includes moving said light beam trace with approximately constant linear velocity.

25. The method of claim 19, wherein said step of sequentially illuminating each said site with a light beam comprises moving the trace of said light beam on said surface of said electrically conducting material so that the trace follows a serpentine pattern that sequentially illuminates each of said sites.

26. The method of claim 25, wherein said step of moving said light beam trace in an approximately serpentine pattern includes moving said light beam trace with approximately constant linear velocity.

27. The method of claim 19, further comprising the step of providing said electrically conducting material from the class of materials with electrical resistivities of no more than $10^6$ ohm-cm that consists of silicon, germanium, gallium arsenide, polysilicon, aluminum, tungsten, molybdenum, titanium silicide, platinum silicide, palladium silicide, cobalt silicide, zirconium silicide, tantalum silicide, hafnium silicide, niobium silicide, vanadium silicide, nickel silicide, tungsten silicide and molybdenum silicide.

28. The method of claim 19, wherein said step of sequentially illuminating said sites includes providing a light beam with a light wavelength of at most 0.4 $\mu$m.

29. The method of claim 19, further comprising the step of providing an atmosphere above said surface of said electrically conducting material composed of a gas whose particles have a relatively low likelihood of electron attachment thereto.

30. The method of claim 29, wherein said step of providing an atmosphere includes providing said gas from the class of gases consisting of He, Ne, Ar, Kr, Xe and $N_2$.

31. The method of claim 19, wherein said step of illuminating said sites on said surface is performed by causing the light beam trace to define a continuous curve that passes through all of said sites.

32. Apparatus for determining the presence and the thickness, if any, of contaminants at each of a plurality of sites on a surface of an electrically conducting material, the apparatus comprising:

illumination means for sequentially illuminating each site with a light beam having a wavelength component that induces photoemission of electrons in the conducting material;

electron collection means for determining the photoelectron current that emerges from the conducting material that lies beneath each illuminated site; and compensation means for electrically compensating for the appearance of capacitive current at the electron collection means.

33. Apparatus according to claim 32, wherein said compensation means includes a second electron collection means for determining a second current that emerges from a portion of the conducting material that is not illuminated by said light beam and means for subtracting this second current from said current measured by said first electron collection means.

34. Apparatus according to claim 32, further comprising second compensation means for electrically compensating for the appearance of photovoltaic current at said electron collection means.

35. Apparatus for determining the presence and the thickness, if any, of contaminants at each of a plurality of sites on a surface of an electrically conducting material, the apparatus comprising:

illumination means for sequentially illuminating each site with a light beam having a wavelength component that induces photoemission of electrons in the conducting material;

electron collection means for determining the photolectron current that emerges from the conducting material that lies beneath each illuminated site; and compensation means for electrically compensating for the appearance of photovoltaic current at the electron collection means.

36. Apparatus according to claim 35, wherein said compensation means comprises:

second illumination means for sequentially illuminating each said site with a second light beam for which the wavelength components have energies greater than the electron energy gap but less than the electron work function in said conducting material;

excitation means for illuminating each said site by said first light beam and by the second light beam in time intervals that do not overlap; and subtraction means associated with said electron collection means for subtracting the current sensed when a site is illuminated by the second light beam from said current sensed when that site is illuminated by said first light beam.

* * * * *

UNITED STATES PATENT AND TRADEMARK OFFICE
CERTIFICATE OF CORRECTION

PATENT NO.  : 4,998,019
DATED       : March 5, 1991
INVENTOR(S) : Stanley Stokowski et al.

It is certified that error appears in the above-identified patent and that said Letters Patent is hereby corrected as shown below:

Column 6, line 2, "$[r^2 + r_1^2]\theta^2$ = constant" should read -- $[r^2 + r_1^2]\dot{\theta}^2$ = constant --.

Column 7, line 61, "a site 89" should read -- a separate site 89 --.

Claim 8, column 9, line 58, "$[r^2 + r_1^2]\theta^2$ = constant" should read -- $[r^2 + r_1^2]\dot{\theta}^2$ = constant --.

Claim 8, column 9, line 61, "radius r" should read -- radius $r^2$ --.

Signed and Sealed this

Tenth Day of November, 1992

Attest:

DOUGLAS B. COMER

*Attesting Officer*    *Acting Commissioner of Patents and Trademarks*